United States Patent [19]

Warriner

[11] Patent Number: Plant 5,734

[45] Date of Patent: May 6, 1986

[54] ROSE PLANT JACINAL

[75] Inventor: William A. Warriner, Tustin, Calif.

[73] Assignee: Jackson & Perkins Company, Medford, Oreg.

[21] Appl. No.: 656,921

[22] Filed: Oct. 1, 1984

[51] Int. Cl.[4] ..... A01H 5/00

[52] U.S. Cl. ..... Plt./26

[58] Field of Search ..... Plt./26

*Primary Examiner*—James R. Feyrer

*Attorney, Agent, or Firm*—Manford R. Haxton

[57] ABSTRACT

A floribunda rose variety having abundant production of medium length stems bearing deep pink buds comparable to R.H.S. Colour Chart Red 51A, opening to lighter pink blooms, of very little fragrance.

1 Drawing Figure

1

This present invention relates to a new and distinct variety of rose plant of the floribunda class which was originated by crossing the variety Bridal Pink, U.S. Plant Pat. No. 2,851, with the variety Zorina, U.S. Plant Pat. No. 2,321.

The primary objective of this breeding was to produce a new rose variety suitable for production of cut blooms under greenhouse conditions of a color deeper than Bridal Pink. This objective was substantially achieved along with other desirable improvements as evidenced by the following unique combination of characteristics which are outstanding in the new variety and which distinguish it from its parents as well as from all other varieties of which I am aware:

1. Bud color is close to R.H.S. Colour Chart Red 51A;
2. A vigorous plant producing medium stem lengths;
3. Relatively flat open flower of 20–25 petals;
4. Good resistance to rose powdery mildew;
5. Long prickles, slightly hooked downward when mature;
6. Very slight fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:

*Seed parent.*—Bridal Pink, U.S. Plant Pat. No. 2,851.

*Pollen parent.*—Zorina, U.S. Plant Pat. No. 2,321.

Classification:

*Botanical.*—Rosa hybrid.

*Commercial.*—Floribunda.

FLOWER

Observations made from specimens grown in a greenhouse at Irvine, Calif. in August.

2

Blooming habit: Continuous.

Bud:

*Size.*—1" when petals start to unfurl.

*Form.*—Long.

*Color.*—When sepals first divide, Red 51A; when half blown, upper side of petals Red 55A; lower side of petals Red 55A.

*Sepals.*—Color: Green 138B. Three appendaged sepals normally appendaged. Two appendaged sepals hairy edged.

*Receptacle.*—Color: Green 138B. Shape: Funnel. Size: Long, small, slender. Surface: Smooth.

*Peduncle.*—Length: Medium. Surface: Slightly prickly, glandular. Color: Light green. Strength: Stiff, erect, slender.

*Opening.*—Petals fold out with very little curling of edges.

Open bloom:

*Size.*—Medium. Average open size 3¼".

*Borne.*—Singly, or several together.

*Stems.*—Medium to short.

*Form.*—When first open, flat. Permanence: Retains its form to the end.

*Petalage.*—Number of petals under normal conditions: 20–25.

*Color.*—Center of flower: Upper side of petals, Red 55B; reverse side of petals, 55B. Base of petals, Near White. Major color: In ordinary dictionary term — Pink Equivalent to R.H.S. Red 55B.

*Discoloration.*—General tonality at end of third day: Slightly lighter to Red 55C.

*Fragrance.*—Slight.

Petals:

*Texture.*—Thick.

*Shape.*—Nearly round.

*Form.*—Tips very slightly recurved.

*Arrangement.*—Imbricated. Petaloids in center, few, large.

*Persistence.*—Drop off cleanly.

*Lastingness.*—On the plant, long. As cut flower, long.

Reproductive parts:

*Anthers.*—Medium. Color: Yellow. Arrangement: Regular around styles.

*Filaments.*—Color: Yellow-Green 150D.

*Pollen.*—Lemon Yellow.

*Styles.*—Color: Red Purple 57A.

*Stigmas.*—Color: White.

PLANT form: Bush.

Growth: Very vigorous, multi-branching.

Foliage: Number of leaflets on normal mid-stem leaves: 5–7.

*Size.*—Large.

*Quantity.*—Normal.

*Color.*—New foliage: Greyed Purple 184. Old foliage: Generally near Green 131A.

Leaflets:

*Shape.*—Oval pointed.

*Texture.*—Leathery.

*Edge.*—Serrated.

*Serration.*—Single, small.

*Petiole.*—Rachis: Color: Reddish, Underside: With prickles.

*Stipules.*—Long, bearded.

*Disease resistance.*—Resistant to mildew, under normal growing conditions at Irvine, Calif.

Wood:

*New wood.*—Color: Light green. Bark: Smooth.

*Old wood.*—Color: Green. Bark: Smooth.

Prickles:

*Quantity.*—On main canes from base: Many. On laterals from main canes: Many.

*Form.*—Long, hooked downward.

*Color when young.*—Brown.

I claim:

1. A new and distinct variety of rose plant of the floribunda class, substantially as herein shown and described, characterized particularly as to novelty by the unique combination of abundant production of medium length stems bearing deep pink buds comparable to R.H.S. Colour Chart Red 51A, opening to lighter pink blooms, of very little fragrance.

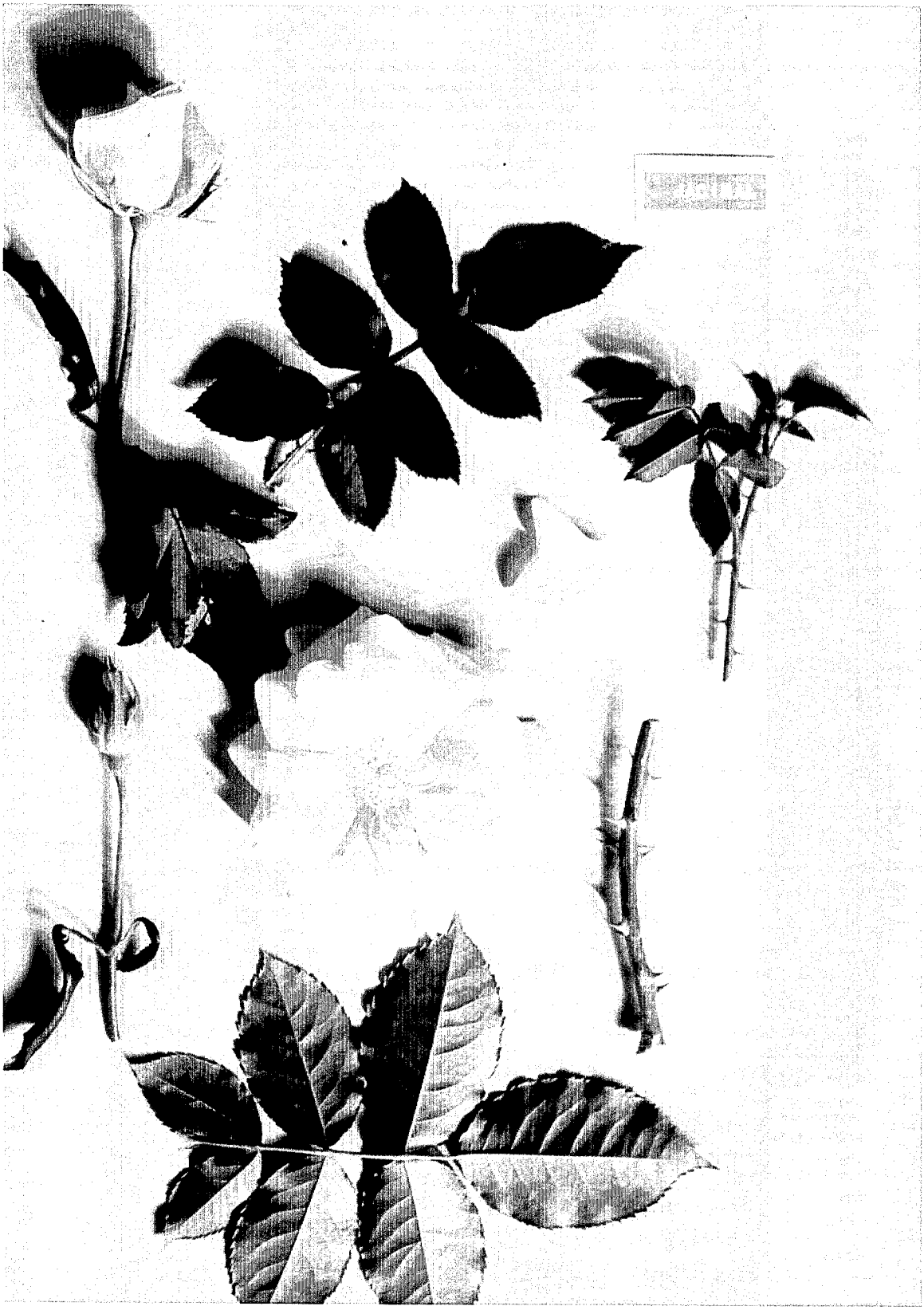

* * * * *